United States Patent
Kweon et al.

(10) Patent No.: US 11,737,839 B2
(45) Date of Patent: Aug. 29, 2023

(54) METHOD AND APPARATUS FOR TRAINING MACHINE LEARNING MODEL FOR DETERMINING OPERATION OF MEDICAL TOOL CONTROL DEVICE

(71) Applicant: MEDIPIXEL, INC., Seoul (KR)

(72) Inventors: Jihoon Kweon, Gyeonggi-do (KR); Young-Hak Kim, Seoul (KR); Kyung Hwan Kim, Seoul (KR); Chae Hyeuk Lee, Gyeonggi-do (KR); Kyo Seok Song, Seoul (KR)

(73) Assignee: MEDIPIXEL, INC., Seoul (KR)

( * ) Notice: Subject to any disclaimer, the term of this patent is extended or adjusted under 35 U.S.C. 154(b) by 0 days.

(21) Appl. No.: 17/798,876

(22) PCT Filed: Jun. 12, 2020

(86) PCT No.: PCT/KR2020/007641
§ 371 (c)(1),
(2) Date: Aug. 10, 2022

(87) PCT Pub. No.: WO2021/162181
PCT Pub. Date: Aug. 19, 2021

(65) Prior Publication Data
US 2023/0105387 A1     Apr. 6, 2023

(30) Foreign Application Priority Data

Feb. 10, 2020   (KR) .................. 10-2020-0015859

(51) Int. Cl.
*G06N 20/00*   (2019.01)
*A61B 34/30*   (2016.01)
(Continued)

(52) U.S. Cl.
CPC ............. *A61B 34/30* (2016.02); *G06N 20/00* (2019.01); *A61B 2034/107* (2016.02); *A61B 2034/2065* (2016.02); *A61B 2034/303* (2016.02)

(58) Field of Classification Search
CPC .............. A61B 34/30; A61B 2034/107; A61B 2034/2065; A61B 2034/303;
(Continued)

(56) References Cited

U.S. PATENT DOCUMENTS

| 2007/0270692 A1 | 11/2007 | Barbu et al. |
| 2007/0276216 A1 | 11/2007 | Beyar et al. |
| 2019/0150869 A1* | 5/2019 | Passerini ............... A61B 6/481 |

FOREIGN PATENT DOCUMENTS

| KR | 10-2013-0137435 | 12/2013 |
| KR | 10-2016-0012537 | 2/2016 |

(Continued)

OTHER PUBLICATIONS

Behr T. et al., "Deep Reinforcement Learning for the Navigation of Neurovascular Catheters", *Biomed. Eng.*, 5:(1)5-8 (2019).
(Continued)

*Primary Examiner* — Charlotte M Baker
(74) *Attorney, Agent, or Firm* — MARSHALL, GERSTEIN & BORUN LLP

(57) ABSTRACT

A method for training, by a processor, a machine learning model for determining an operation of a medical tool control device may comprise the steps of: obtaining an operation command to move a medical tool of the medical tool control device on the basis of the machine learning model from guide data generated using a blood vessel image; generating evaluation data of a position to which the distal end of the medical tool has been moved according to the operation command in a blood vessel image; and updating a parameter
(Continued)

of the machine learning model by using the evaluation data, so as to train the machine learning model.

17 Claims, 8 Drawing Sheets

(51) Int. Cl.
*A61B 34/10* (2016.01)
*A61B 34/20* (2016.01)

(58) Field of Classification Search
CPC ........ A61B 2034/301; A61B 2090/376; A61B 2090/374; A61B 34/20; A61B 34/10; A61B 2034/102; A61B 2034/105; G06N 20/00; G06N 3/08; A61M 25/0113; A61M 2025/0166; G09B 23/303
USPC ........................................................ 382/128
See application file for complete search history.

(56) References Cited

FOREIGN PATENT DOCUMENTS

| KR | 10-2017-0049172 | 5/2017 |
| WO | WO-2018/156460 | 8/2018 |

OTHER PUBLICATIONS

Hoda S. et al., "Navigation of guidewires and catheters in the body during intervention procedures: a review of computer-based models", *J. Med. Imaging*, 5:(1) 10 pages (2018).
Pusch T. et al., "Towards using SOFA to train a controller for neurovascular catheter interventions", SWS19—SOFA Week Symposium, 5 pages (2019).
International Search Report and Written Opinion for PCT/KR2020/007641, dated Nov. 4, 2020.
Office Action issued in KR 10-2020-0015859, dated May 12, 2021.
Notice of Grant issued in KR 10-2020-0015859, dated Jul. 7, 2021.

* cited by examiner

METHOD AND APPARATUS FOR TRAINING MACHINE LEARNING MODEL FOR DETERMINING OPERATION OF MEDICAL TOOL CONTROL DEVICE

TECHNICAL FIELD

The following description relates to a method and an apparatus for training a machine learning model for determining an operation of a medical tool control device.

BACKGROUND ART

When treating cardiovascular, cerebrovascular, and peripheral blood vessels, an interventional procedure that inserts a stent and the like using a guide wire and a catheter is widespread. The guide wire is a tool for setting a path for transporting a stent and the like into the blood vessel through the catheter, and in order to transport the guide wire to the end of the blood vessel with diseases, visual information based on medical images such as angiography, tactile information based on fine feeling of the hand, and the like are utilized.

Recently, remote robots and the like have been developed to reduce the physical burden of an operator, such as radiation exposure, and to precisely control surgical tools. Although surgical robots have been commercialized through the FDA, learning to be adapted to new tools is required to perform simple surgical operations. Even if the corresponding operation, such as moving the guide wire backwards or rotating the guide wire at a predetermined angle, is not directly performed, functions that the robot takes over are being added, but the proportion of the operations in the surgical procedure is small.

Prior Art Document (Patent Document 1) KR Patent Application Publication No. 2017-0049172 (published on May 10, 2017)

DISCLOSURE OF THE INVENTION

Technical Solutions

According to an aspect, there is provided a method for training, by a processor, a machine learning model for determining an operation of a medical tool control device may include the steps of: obtaining an operation command to move a medical tool of the medical tool control device on the basis of the machine learning model from guide data generated using a blood vessel image; generating evaluation data of a position to which the distal end of the medical tool has been moved according to the operation command in a blood vessel image; and updating a parameter of the machine learning model by using the evaluation data, so as to train the machine learning model.

According to an aspect, the generating of the evaluation data may include applying a compensation value calculated according to a comparison result between the position to which the distal end of the medical tool has been moved in the blood vessel image and the guide data to the evaluation data.

The guide data may include information about a position of the distal end of the medical tool together with at least one of a middle target point, an access restriction point, and a destination point in a patch image corresponding to at least a partial area of the blood vessel image, and the generating of the evaluation data may include applying a first group compensation value to the evaluation data in response to a case where the distal end of the medical tool reaches one of the destination point and the middle target point in the blood vessel image.

The applying of the first group compensation value may include applying a first compensation value to the evaluation data in response to the case of reaching the destination point, and applying a second compensation value smaller than the first compensation value to the evaluation data in response to the case of reaching the middle target point.

The generating of the evaluation data may include applying a second group compensation value to the evaluation data in response to a case where the distal end of the medical tool reaches an access restriction point and a case where the distal end of the medical tool has been moved into a section between the areas.

The applying of the second group compensation value may include applying a third compensation value to the evaluation data in response to the case of reaching the access restriction point, and applying a fourth compensation value having a smaller absolute value than the first compensation value in response to the case of moving into the section between the areas.

The training of the machine learning model according to an example embodiment may include calculating an estimated evaluation value associated with an operation command output from a guide image corresponding to a current time frame by using the machine learning model, calculating a measured evaluation value (target evaluation value) from a guide image corresponding to a next time frame after the medical tool has been moved according to the operation command output in the current time frame, and determining a parameter to update the machine learning model by using the estimated evaluation value and the target evaluation value.

The obtaining of the operation command of the medical tool control device according to an aspect may include calculating an expectation value to reach a destination point for each of candidate operation commands that may be performed by the medical tool control device by using at least a part of the machine learning model, and outputting an operation command having the highest expectation value among the candidate operation commands by using the remaining machine learning model.

Further, the method for training the machine learning model may include calculating a blood vessel structure from the blood vessel image, setting a middle target point and an access restriction point based on the blood vessel structure and the destination point, obtaining an entire guide image in which the destination point, the middle target point, and the access restriction point are set, extracting partial guide information from the entire guide image based on the position of the distal end of the medical tool, and determining the operation command based on the machine learning model from the partial guide information.

Advantageous Effects

According to the method for training the machine learning model for determining the operation of the medical tool control device according to an example embodiment, it is possible to improve the speed of the medical tool control device by controlling the medical tool control device using an artificial neural network and learning the medical tool control device using the result.

Further, it is possible to numerically evaluate a series of operation commands of the medical tool control device by generating a destination point, a middle target point, and an access restriction point.

BEST MODE FOR CARRYING OUT THE INVENTION

Figure 1:
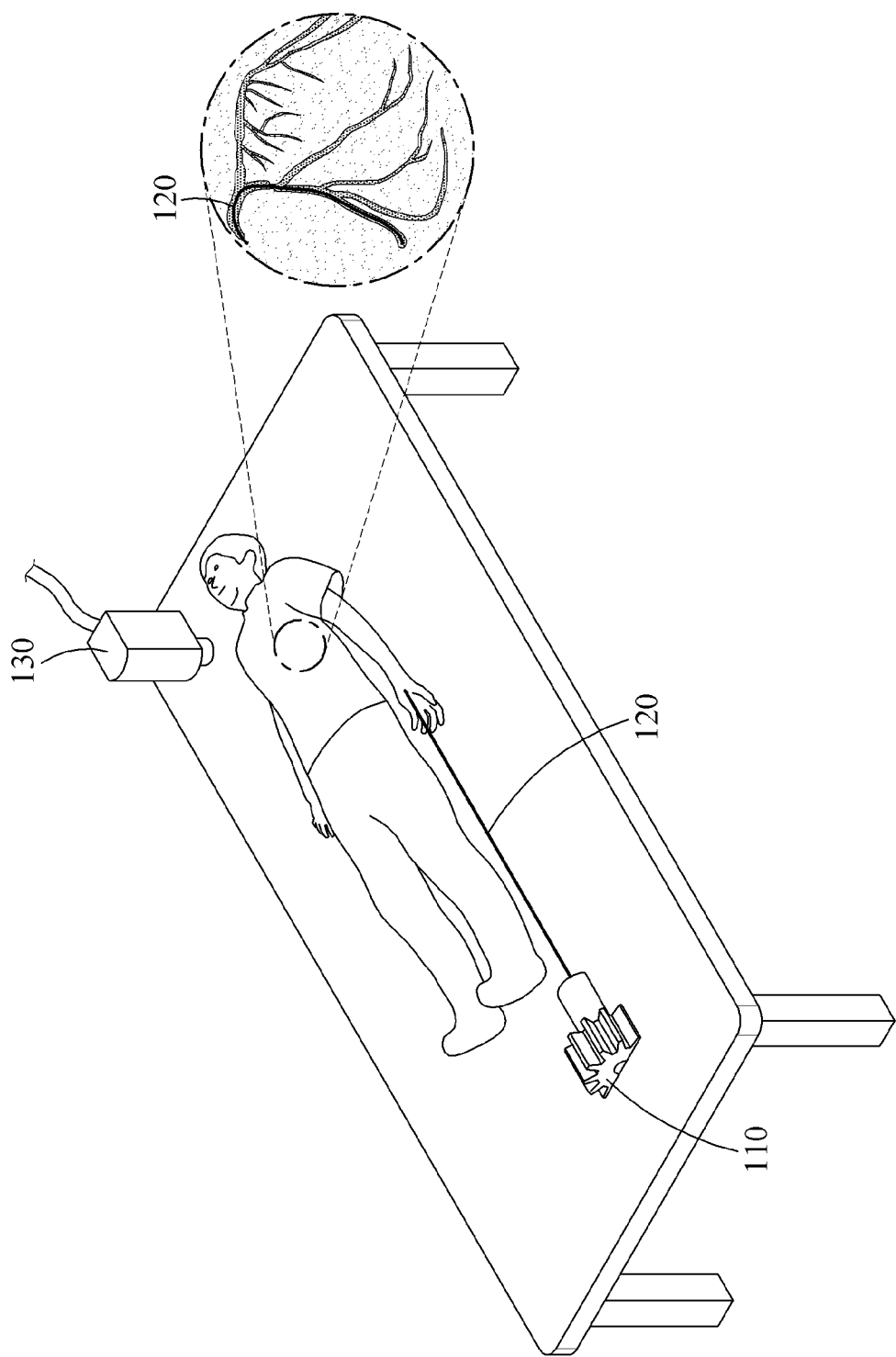
FIG. 1 is a diagram illustrating an operation of a medical tool control device according to an example embodiment.

Specific structural or functional descriptions of example embodiments will be disclosed for purposes of only examples, and may be changed and implemented in various forms. Accordingly, the example embodiments are not limited to a specific disclosure form, and the scope of the present specification includes changes, equivalents, or substitutes included in the technical spirit.

Terms such as first or second may be used to describe various components, but these terms should be interpreted only for the purpose of distinguishing one component from other components. For example, a first component may be referred to as a second component, and similarly, the second component may be referred to as the first component.

It should be understood that, when it is described that a component is "connected" to the other component, the component may be directly connected to or access the other component or a third component may be present therebetween.

Singular expressions used herein include plurals expressions unless they have definitely opposite meanings in the context. In the present specification, it should be understood that the term "including" or "having" indicates that a feature, a number, a step, an operation, a component, a part, or the combination thereof described in the specification is present, but does not exclude a possibility of presence or addition of one or more other features, numbers, steps, operations, components, parts, or combinations thereof, in advance.

If it is not contrarily defined, all terms used herein including technological or scientific terms have the same meanings as those generally understood by a person with ordinary skill in the art. Terms which are defined in a generally used dictionary should be interpreted to have the same meaning as the meaning in the context of the related art, and are not interpreted as an ideal meaning or excessively formal meanings unless clearly defined in the present specification. Hereinafter, example embodiments will be described in detail with reference to the accompanying drawings. Like reference numerals illustrated in the respective drawings designate like members.

FIG. 1 is a diagram illustrating an operation of a medical tool control device according to an example embodiment.

A medical tool control device 110 according to an example embodiment may move a medical tool 120 to a blood vessel destination point according to a driving command by a processor. For example, the medical tool control device 110 may move the distal end of the medical tool 120 to the blood vessel destination point. The medical tool control device 110 may be implemented as a robot for performing surgery, and for example, a robot for controlling the medical tool for cardiovascular intervention.

The medical tool 120 is a member inserted into a blood vessel, and may include a medical tool disposed on the distal end of the medical tool 120 and a medical wire connecting the medical tool to a driving unit. The medical wire may include, for example, a catheter or a guide wire. The guide wire may refer to a medical wire used for inserting and guiding the aforementioned medical tool to a target site of the blood vessel. The medical tool may be a surgical tool operated according to the control of a doctor, for example, an introducer kit.

The medical tool control device 110 may determine the above-described driving command using a blood vessel image. For example, the medical tool control device 110 may output a driving command from the blood vessel image by performing a calculation according to the machine learning model. The machine learning model is a model designed and trained to receive the blood vessel image and output guide data, and may be implemented as, for example, a neural network model. However, the input of the machine learning model is not limited to the blood vessel image, and may also be a blood vessel structure image and guide data. The guide data may represent data in which guide information is mapped to the blood vessel image or the blood vessel structure image. The blood vessel structure image is an image in which a specific blood vessel is extracted from the blood vessel image, and may be an image obtained by preprocessing the blood vessel image. The blood vessel structure image will be described with reference to FIG. 3 below. The blood vessel image may be an image generated using corona angiography (hereinafter, CAG) or magnetic resonance imaging (hereinafter, MRI). In the blood vessel image, not only the blood vessel but also the medical tool 120 may be photographed.

The guide information is information for guiding the movement and rotation of the medical tool 120, and may include, for example, information about an area in which the medical tool 120 should depart, an area through which the medical tool 120 should pass, and a destination point in the blood vessel. The information on each area may include image coordinates in the blood vessel structure image of the corresponding area, but is not limited thereto. According to an example embodiment, guide information may be visually mapped to the blood vessel structure image. For example, a graphic object corresponding to each target area may be visualized in the blood vessel structure image, and the blood vessel structure image in which the target area is visualized may be represented as a guide image.

The processor of the medical tool control device 110 may determine to drive the medical tool 120 based on the result of analyzing the blood vessel image. The processor may determine a driving command by using at least one of the blood vessel image, the blood vessel structure image, and the guide data. The driving command may represent a command for operating the driving unit connected to the medical tool 120 to move and rotate the medical tool 120. The driving command may be, for example, a forward command, a backward command, a clockwise rotation command, and a counterclockwise rotation command, but is not limited thereto.

The medical tool control device 110 may analyze the received blood vessel image to generate guide data, and the medical tool control device 110 may determine a driving command from the generated guide data. For example, the medical tool control device 110 may select, as an operation command, one of a forward command, a backward command, a clockwise rotation command, and a counterclockwise rotation command from the guide data. The driving unit of the medical tool control device 110 may be driven according to the selected operation command. For example, the driving unit may move the medical tool 120 forward in response to the forward command. The driving unit may retract the medical tool 120 in response to the backward command. The driving unit may rotate the guide wire clockwise based on the longitudinal axis of the guide wire in response to the clockwise rotation command. The driving unit may rotate the guide wire counterclockwise based on the longitudinal axis of the guide wire in response to the counterclockwise rotation command.

Accordingly, the medical tool control device 110 determines a series of operation commands using the guide data generated by analyzing the blood vessel image, thereby moving the distal end of the medical tool 120 to the area to be guided by the guide data. The medical tool control device 110 may move the distal end of the medical tool 120 to a final destination point by repeating the operation determination using the guide data. After the distal end of the medical tool 120, for example, the medical tool reaches the destination point, the medical tool may perform a surgical operation under the control of the doctor.

Referring to FIG. 1, after the medical tool 120 is inserted through the blood vessel of the wrist of a patient, the medical tool control device 110 may guide and move the medical tool 120 to a target blood vessel. However, the medical tool 120 is not limited to being inserted through the blood vessel of the wrist of the patient, and may be inserted through the blood vessel of the lower extremity of the patient.

Figure 2:
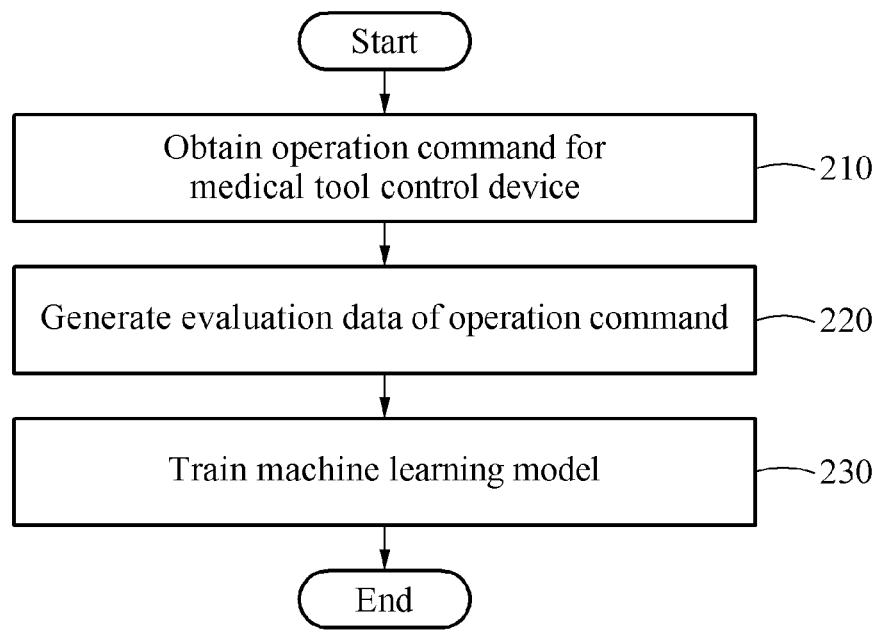
FIG. 2 is a flowchart illustrating a method for training a machine learning model according to an example embodiment.

FIG. 2 is a flowchart illustrating a method for training a machine learning model according to an example embodiment.

In step 210, a processor for training a machine learning model according to an example embodiment may obtain an operation command of a medical tool control device. The processor may obtain an operation command for moving the medical tool of the medical tool control device based on the machine learning model from guide data generated using a blood vessel image. The guide data may include information about a position of the distal end of the medical tool in the blood vessel image together with at least one of a middle target point, an access restriction point, and a destination point in a patch image corresponding to at least a partial area of the blood vessel image. An example embodiment of generating guide data will be described below in detail with reference to FIG. 3.

In step 220, the processor according to an example embodiment may generate evaluation data of the obtained operation command. The evaluation data may be evaluation data on the position to which the distal end of the medical tool has been moved according to the operation command in the blood vessel image. The processor may generate the evaluation data by applying a first group compensation value or a second group compensation value according to whether one of the middle target point, the access restriction point, and the destination point is reached in the blood vessel image including the guide data. That is, the processor may generate the evaluation data by applying a compensation value calculated according to a comparison result between the guide data and the position to which the distal end of the medical tool has been moved in the blood vessel image. The compensation value may be set to different values based on a position, a time, and the number of control commands.

In step 230, the processor according to an example embodiment may train the machine learning model by updating a parameter of the machine learning model using the evaluation data.

Figure 3:
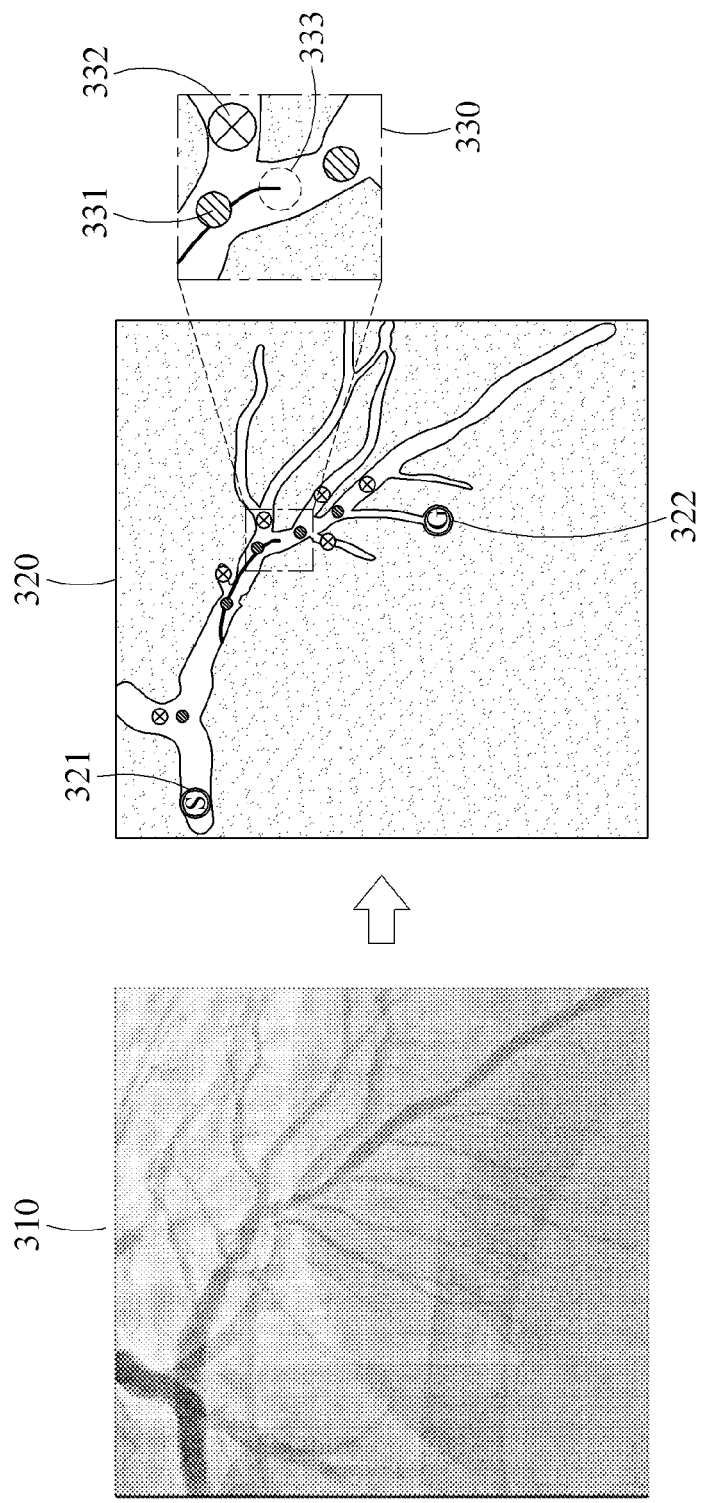
FIG. 3 is a diagram illustrating generating guide data from a blood vessel structure image according to an example embodiment.

FIG. 3 is a diagram illustrating generating guide data from a blood vessel structure image according to an example embodiment.

According to an example embodiment, the processor may obtain a blood vessel structure image from a blood vessel image 310 and generate guide data based on blood vessel branch area information of the blood vessel structure image. However, the present invention is not limited thereto, and the processor may receive an entire guide image 320 in which the guide information is generated in the blood vessel structure image. The guide information may include a destination point 322 to guide and move the distal end of the medical tool by the medical tool control device, a middle target point 331 on a path from a start area 321 to the destination point 322, and an access restriction point 332 which is an area to be excluded by the guide of the distal end of the medical tool.

The blood vessel structure image may be an image in which a blood vessel identified from the blood vessel image 310 and a structure and a connection relationship of the blood vessel are displayed. The processor according to an example embodiment may generate a blood vessel structure image by dividing a blood vessel area and a background area from the blood vessel image 310 by using an edge detecting method. Illustratively, the edge detecting method may detect, as an edge, an area in which the grayscale levels of an arbitrary pixel and neighboring pixels rapidly change, but is not limited thereto, and may also be another method of detecting an edge between the blood vessel area and the background area.

The processor according to an example embodiment may extract a target blood vessel from the image divided into the blood vessel area and the background area, based on a thickness of the blood vessel in the blood vessel area and a grayscale level in the image. For example, when it is desired to extract a cardiovascular system as a target blood vessel, the blood vessel image 310 may include not only the cardiovascular system but also blood vessels other than the cardiovascular system. In the case of using the CAG, a blood vessel in which a contrast medium is injected may have a lower grayscale level than a blood vessel in which the contrast medium is not injected, and a blood vessel in which the medical tool is movable may have a greater thickness than a blood vessel in which the medical tool is not movable. Accordingly, for example, in order to extract the cardiovascular system, the processor may determine a blood vessel having a thickness greater than a threshold thickness and a grayscale level lower than a threshold grayscale level as the cardiovascular system in the blood vessel area. However, the present invention is not limited thereto, and the processor may distinguish a blood vessel area to be extracted using a trained machine learning model.

According to an example embodiment, the processor may extract partial guide information 330 based on the position of the distal end of the medical tool from the entire guide image 320 in which the guide information is generated in the blood vessel structure image. The processor may determine an operation command of the medical tool control device based on the guide information included in the partial guide information 330. That is, the processor may determine an operation command of the medical tool control device based on the partial guide information 330 focused on the position 333 of the distal end of the medical tool and the positions of the middle target point 331 and the destination point 322 to be guided by the distal end of the medical tool around the distal end of the medical tool. The processor may extract new partial blood vessel information whenever the medical tool is moved by performing one operation command by the driving unit of the medical tool control device. The processor may compare partial blood vessel information corresponding to the current time frame with new partial blood vessel information corresponding to the next time frame after one operation command is performed, and may update a parameter of the machine learning model based on the comparison result.

Figure 4:
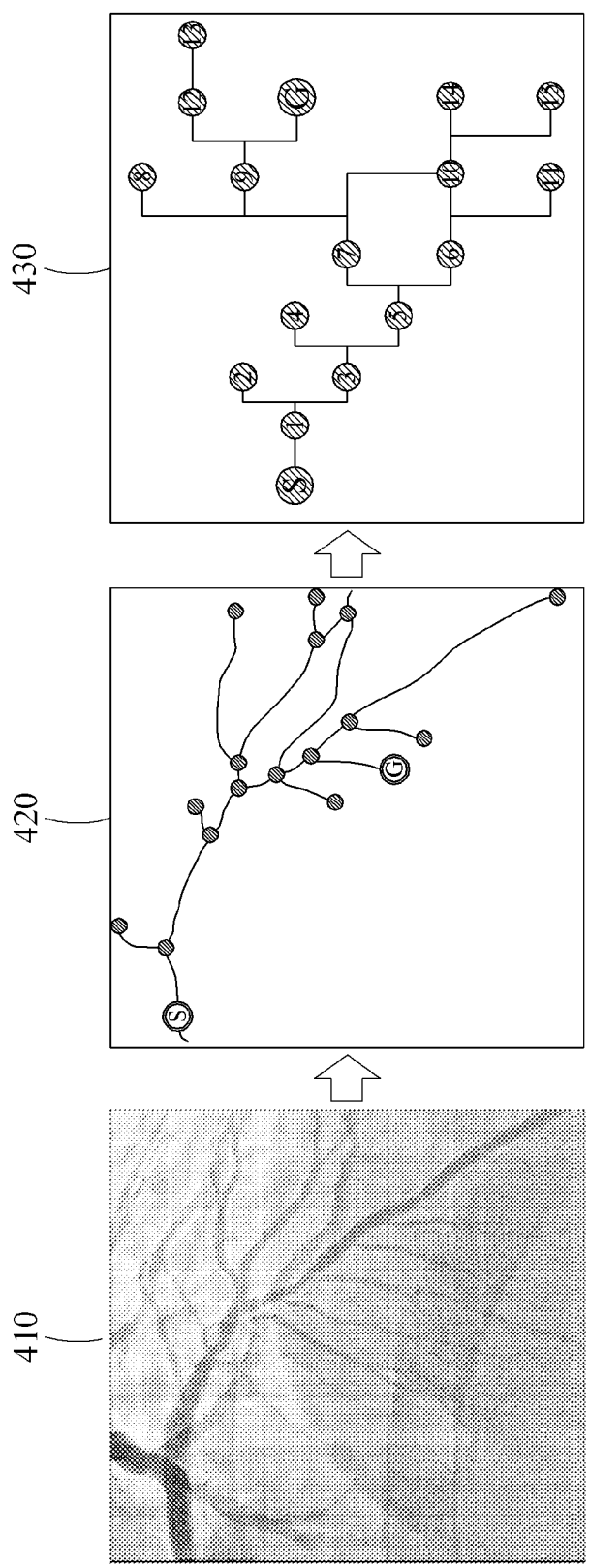
FIG. 4 is a diagram illustrating generating blood vessel structure data from a blood vessel image according to an example embodiment.

FIG. 4 is a diagram illustrating generating guide data by generating blood vessel structure data from a blood vessel image according to an example embodiment.

The processor according to an example embodiment may generate blood vessel structure data from the blood vessel image, and generate guide data based on the blood vessel structure data. The processor may extract a blood vessel area from a blood vessel image 410, and may recognize a position where a blood vessel branch starts in the blood vessel area as a blood vessel branch area. In a vascular simplified image 420 illustrated in FIG. 4, the recognized blood vessel is marked as a solid line, and a position identified as the blood vessel branch area and the distal area of the blood vessel are marked as nodes.

The processor may generate blood vessel structure data 430 based on the branch area identified from the vascular simplified image 420 and connection information of the branched blood vessel. According to an example embodiment, the processor may generate node data indicating the branch area and edge data indicating the branched blood vessel. Since the branched blood vessel is connected to two different branch areas, the processor may connect two node data to one edge data, and the node data may map edge data corresponding to the number of branched blood vessels. The connection information of the branch area and the branched blood vessel may be information indicating a connection relationship between the branch area and the branched blood vessel, and may be generated using edge data mapped to the node data and node data that is a connection target of the edge data. The processor may data-structure the blood vessel based on the connection information. For example, the processor may generate a tree structure in which the nodes and the edges are connected by using a branch area closest to a blood vessel introduction part as a root node. The root node may be a node corresponding to the highest branch area, but may be a node corresponding to the start area.

Thereafter, the processor may search for a path from the root node corresponding to the start area to the node corresponding to the destination point based on the blood vessel structure data 430, and may set areas in the blood vessel image corresponding to the nodes on the path as middle target points. The processor may set all modes except for the node set as the middle target point among all nodes of the blood vessel structure data as the access restriction point.

Figure 5:
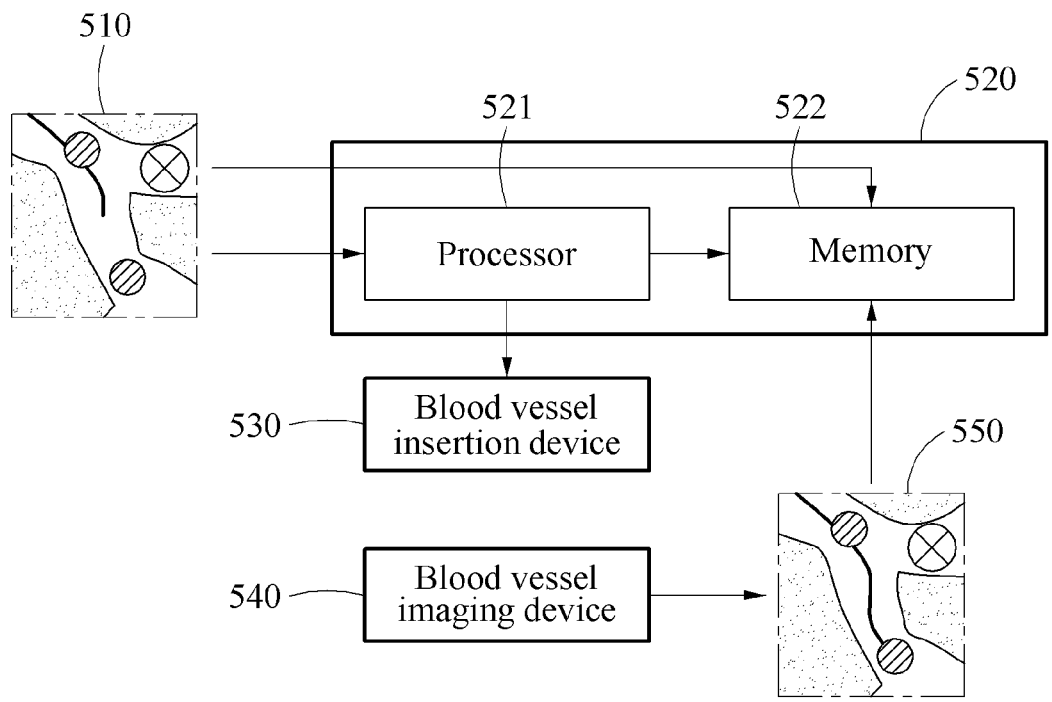
FIG. 5 is a block diagram illustrating determining an operation command of the medical tool control device on the basis of the machine learning model according to an example embodiment.

The processor, which determines the operation command of the medical tool control device based on the machine learning model according to an example embodiment and trains the machine learning model based on the determined operation command, may consist of one or more physical processors. That is, the determining of the operation command of the medical tool control device and the training of the machine learning model may be implemented in a device consisting of a single housing, and each function may be implemented as a function distinguished from each other in one or more processors. However, the present invention is not limited thereto, and the determining of the operation command and the training of the machine learning model may be implemented by a processor in a separate housing. In addition, a memory for determining an operation command and a memory for training a machine learning model may be included in separate housing devices, but may be included in one housing device. FIG. 5 may illustrate operations of the processor and the memory with respect to the determining of the operation command, and FIG. 6 may illustrate operations of the processor and the memory with respect to the training of the machine learning model.

FIG. 5 is a block diagram illustrating determining an operation command of the medical tool control device on the basis of the machine learning model according to an example embodiment.

According to an example embodiment, a processor 521 of a device 520 for determining an operation command may receive partial guide information 510 of a current time frame. The processor 521 may determine an operation command for guiding the distal end of the medical tool to the middle target point or the destination point based on the position of the distal end of the medical tool, and the positions of the middle target point, the destination point, and the access restriction point. The processor 521 may transmit an operation command to a medical tool control device 530. A memory 522 according to an example embodiment may store the partial guide information 510 of the current time frame and an operation command in the current time frame determined by the processor 521.

The medical tool control device 530 may perform an operation command provided from the processor 521 while gripping the medical tool. For example, as described above in FIG. 1, the medical tool control device 530 may move or rotate a medical tool (e.g., a guide wire and a medical tool) by driving a driving unit according to the operation command.

After the medical tool control device 530 executes the operation command, the processor 521 and the memory 522 may receive partial guide information 550 of the next time frame related to the distal end of the moved medical tool. For example, a blood vessel imaging device 540 may output the partial guide information 550 corresponding to the next time frame in the next time frame after the medical tool control device 530 performs the operation command in the current time frame. The processor 521 may determine an operation command of the medical tool control device 530 in the next time frame based on the partial guide information 550 corresponding to the next time frame. The memory 522 may store the partial guide information 550 corresponding to the next time frame as one set mapped together with the partial guide information 510 corresponding to the current time frame. In the present specification, the blood vessel information about the current time frame and the next time frame has been mainly described as the partial guide information 510 and 550, but is not limited thereto and may be a blood vessel image or entire guide information about the current time frame and the next time frame.

According to an example embodiment, the processor 521 may determine an operation command by using the machine learning model. For example, the processor 521 may calculate an expectation value to reach a destination point for each of the candidate operation commands that may be performed by the medical tool control device 530 using at least a part of the machine learning model. The processor 521 may output an operation command having the highest expectation value among the candidate operation commands by using the remaining model of the machine learning model. The medical tool control device 530 may perform an operation command output by the machine learning model.

According to another example embodiment, the processor 521 may calculate directly an operation value by using the machine learning model. For example, the processor 521 may output an operation command from input data (e.g., partial guide information) by using the machine learning model. According to yet another example embodiment, the processor 521 may calculate a change rate of an expectation value for each of the candidate operation commands by using the machine learning model. The processor 521 may determine the operation command by calculating an operation value having the largest change rate of the expectation value among the candidate operation commands. However, the determining of the operation command using the machine learning model by the processor 521 is not limited to those described above, and all machine learning models capable of determining the operation command from the blood vessel image may be used.

Figure 6:
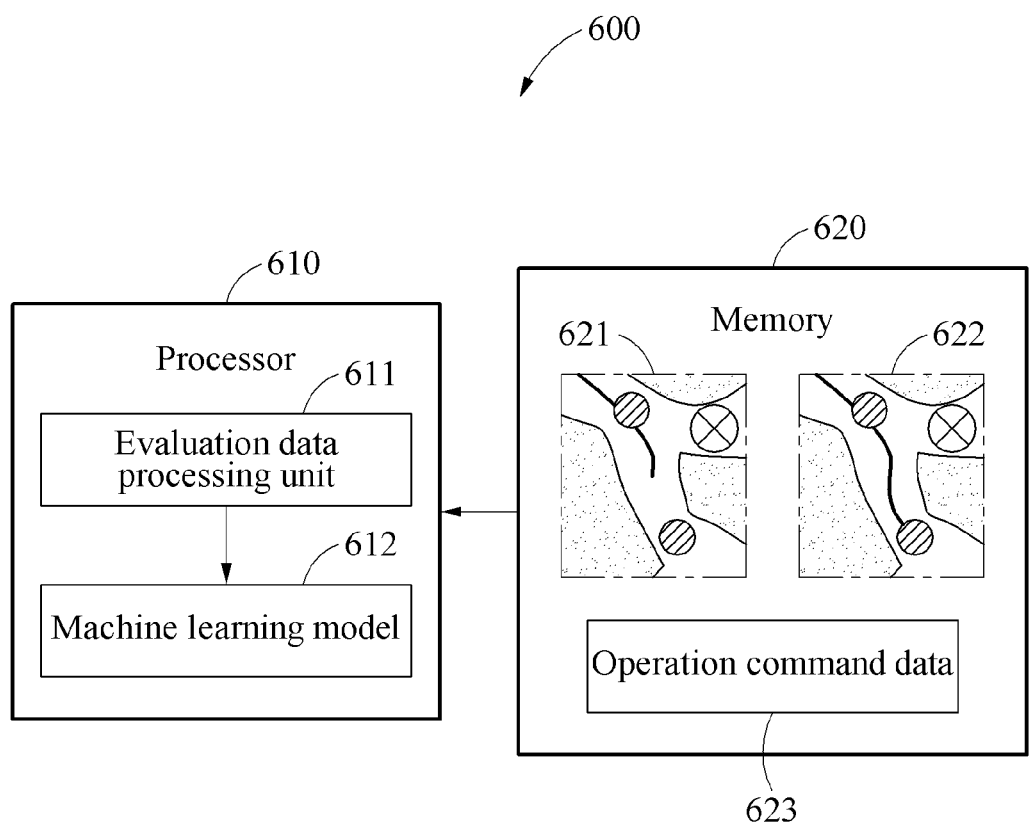
FIG. 6 is a block diagram illustrating training the machine learning model according to an example embodiment.

FIG. 6 is a diagram illustrating extracting partial guide information according to an example embodiment.

An apparatus 600 for training a machine learning model 612 according to an example embodiment may include a processor 610 and a memory 620. After the medical tool control device performs a series of operation commands, the processor 610 may receive, from the memory 620, partial guide information 621 of a first time frame, partial guide information 622 of a second time frame, which is a next time of the first time, and operation command data 623 that has been transmitted to the medical tool control device at the first time. For example, if the first time frame is a t-th frame, the second time frame may be a t+1-th frame, in which t may be an integer of 1 or more. The time unit of each time frame may be determined according to a design.

An evaluation data calculation unit 611 of the processor 610 may calculate evaluation data based on the partial guide information 622 of the second time frame. The machine learning model 612 may receive the partial guide information 621 of the first time frame, the partial guide information 622 of the second time frame, the operation command data 623 at the first time, and the evaluation data as training data to update parameters.

According to an example embodiment, the training data may be a combination of the partial guide information 621 and 622 of the first time frame and the second time frame generated when a series of operation commands and each operation command are output after a series of operations are performed. However, the training data is not limited thereto, and may include combinations of the partial guide information 621 and 622 of the first time frame and the second time frame generated whenever respective operation commands are performed. That is, in response to the performing of each operation command by the medical tool control device, the memory 620 may store the operation command data 623, the partial guide information 621 of a time frame before the operation command is performed, and the partial guide information 622 of a time frame after the operation command is performed may be stored as one training set.

The processor 610 according to an example embodiment may compensate the evaluation data by applying a compensation value calculated according to a comparison result between the position to which the distal end of the medical tool has been moved and the guide data to the evaluation data. The applying of the compensation value according to the guide data and the position of the distal end of the medical tool will be described in detail with reference to FIG. 7.

The processor 610 may update the machine learning model 612 based on the evaluation data to which the compensation value is applied. The processor 610 may calculate an estimated evaluation value associated with the operation command from a guide image corresponding to the first time frame before the operation command is performed. In addition, the processor 610 may calculate a measured evaluation value from a guide image corresponding to a time frame (e.g., a second time frame) after the distal end of the medical tool has been moved according to the operation command output in the first time frame. The processor 610 may determine a parameter to update the machine learning model 612 by using the estimated evaluation value and the measured evaluation value. According to an example embodiment, the processor 610 may calculate, as the estimated evaluation value, an expectation value calculated by performing the operation command determined by the machine learning model 612 by the medial tool control device in the first time frame. In addition, the processor 610 may calculate a candidate expectation value of each of the candidate operation commands which may be performed by the medical tool control device in the second time frame, and calculate a value obtained by adding evaluation data to the largest candidate expectation value among the candidate operation commands as a measured evaluation value. Here, the expectation value may mean a cumulative compensation expectation value that may be obtained when the medical tool control device performs a series of operation commands. Accordingly, the estimated evaluation value may be a value indicating a cumulative compensation expectation value before the medical tool control device actually performs the operation command. The measured evaluation value may be a value obtained by applying a compensation value obtained by performing the actual operation command to a maximum expectation value in a time frame after the medical tool control device performs the actual operation command.

The processor 610 may calculate a parameter to update the machine learning model 612 based on a loss calculated by using the measured evaluation value and the estimated evaluation value. For example, the processor 610 may update the parameters of the machine learning model 612 such that a difference between the measured evaluation value and the estimated evaluation value as the loss is minimized. The processor 610 may repeat the parameter updating of the machine learning model 612 until the calculated loss is less than a threshold loss. In other words, the processor 610 may learn the machine learning model 612 so that the estimated evaluation value (e.g., a cumulative compensation expectation value estimated between the first time frame and the second time frame) is equal to or similar to the measured evaluation value (e.g., a value obtained by applying the compensation value to the maximum expectation value calculated after the actual operation command is performed).

Figure 7:
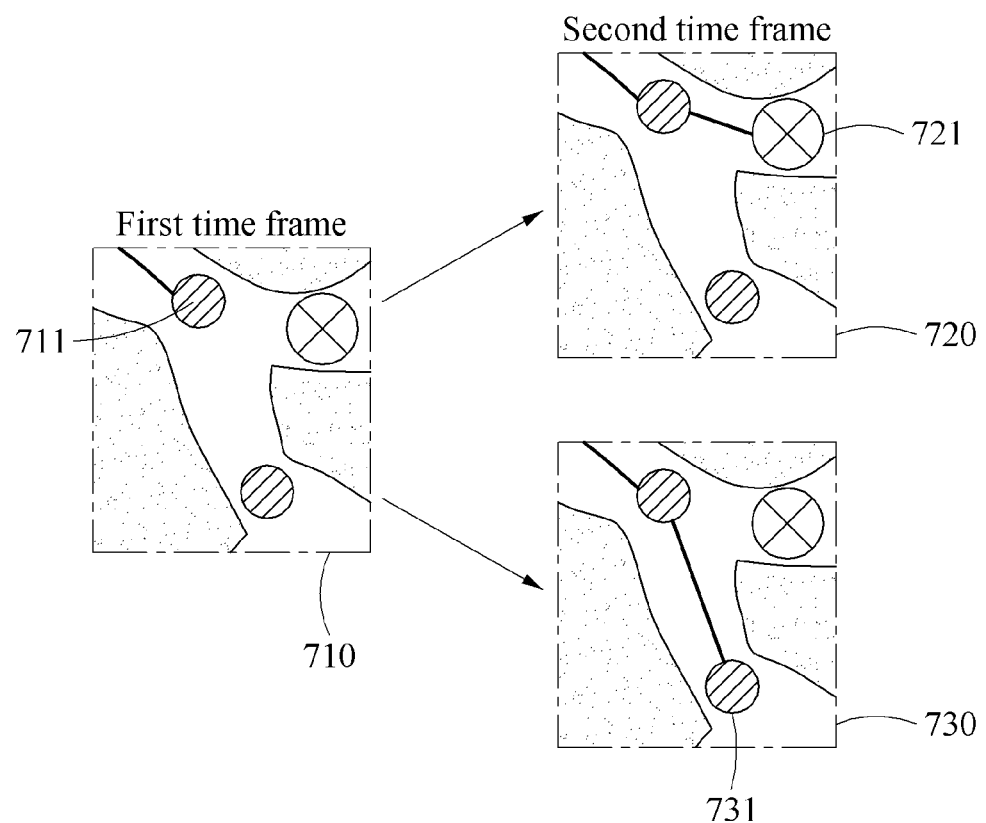
FIG. 7 is a diagram illustrating a guide image corresponding to a current time frame and a guide image corresponding to the next time frame according to an example embodiment.

FIG. 7 is a diagram illustrating a guide image corresponding to a current time frame and a guide image corresponding to the next time frame according to an example embodiment.

The processor according to an example embodiment may apply, to evaluation data, a compensation value calculated according to a comparison result between guide data and a position to which the distal end of the medical tool has been moved in the blood vessel image. The processor may calculate a compensation value by comparing the blood vessel image of the second time frame after the distal end of the medical tool has been moved from the blood vessel image of the first time frame.

The guide data generated from the blood vessel image may include information about a position of the distal end of the medical tool together with at least one of a middle target point, an access restriction point, and a destination point in a patch image corresponding to at least a partial area of the blood vessel image as guide information. The processor according to an example embodiment may calculate a compensation value according to a position to which the distal end of the medical tool has been moved in the blood vessel patch image in which the guide information is visualized.

The processor according to an example embodiment may apply a first group compensation value to the evaluation data in response to a case where the distal end of the medical tool reaches one of the destination point and the middle target point in the blood vessel image. The first group compensation value may vary depending on a type of guide data. For example, the processor may assign a larger first group compensation value to a case where the distal end of the medical tool reaches the destination point than a case where the distal end of the medical tool reaches the middle target point. The processor may apply the first compensation value to the evaluation data in response to the case of reaching the destination point. In response to the case of reaching the middle target point, the processor may apply a second compensation value smaller than the first compensation value to the evaluation data.

In addition, the processor according to an example embodiment may apply a second group compensation value to the evaluation data when the distal end of the medical tool reaches the access restriction point in the blood vessel image or moves into a section between the areas. Although the distal end of the medical tool did not reach any one of the middle target point, the destination point, and the access restriction point, the case of moving into the section between the areas may be a case in which the medical tool control device performs an operation command. The second group compensation value may vary depending on a type of guide data. For example, the processor may assign a larger second group compensation value to a case where the distal end of the medical tool reaches the access restriction point than a case where the distal end of the medical tool moves into the section between the areas. The processor may apply a third compensation value to the evaluation data in response to the case of reaching the access restriction point. The processor may apply a fourth compensation value having a smaller absolute value than the first compensation value in response to the case of moving into the section between the areas.

According to the example embodiment of FIG. 7, the processor may recognize that the distal end of the medical tool has reached a first middle target point 711 in a patch image 710 corresponding to a partial area of the blood vessel image of the first time frame. Accordingly, the processor may determine an operation command of the medical tool control device based on the machine learning model. When the medical tool control device moves the medical tool according to the operation command of the processor, the processor may obtain a first patch image 720 or a second patch image 730 in the second time frame according to a type of operation command.

For example, the first patch image 720 may represent an image obtained when the distal end of the medical tool reaches the access restriction point according to an arbitrary operation command. The processor may determine from the first patch image 720 that the distal end of the medical tool has reached an access restriction point 721. In response to the case where the distal end of the medical tool reaches the access restriction point 721, the processor may apply a second group compensation value corresponding to the access restriction point to the evaluation data.

As another example, the second patch image 730 may represent an image obtained when the distal end of the medical tool reaches a second middle target point 731 according to another operation command. The processor may determine from the second patch image 730 that the distal end of the medical tool has reached the second middle target point 731. In response to the case where the distal end of the medical tool reaches the second middle target point 731, the processor may apply a first group compensation value corresponding to the middle target point to the evaluation data.

For reference, for convenience of description, it has been described that in the first patch image 720 of the second time frame from the patch image 710 of the first time frame, the distal end of the medical tool reaches the access restriction point 721 by one operation command, but it is not limited thereto. According to a distance between the first middle target point 711 and the access restriction point 721, when the distal end of the medical tool reaches from the first middle target point 711 to the access restriction point 721, a plurality of operation commands may be required. Similarly, it has been described that in the second patch image 730 of the second time frame from the patch image 710 of the first time frame, the distal end of the medical tool reaches the second middle target point 731 by one operation command, but it is not limited thereto. According to a distance between the first middle target point 711 and the second middle target point 731, when the distal end of the medical tool reaches from the first middle target point 711 to the second middle target point 731, a plurality of operation commands may also be required. When the distal end of the medical tool does not reach the middle target point by an operation according to one operation command, but moves only into the section between the areas, a negative compensation value may be applied to the evaluation data as described above.

Figure 8:
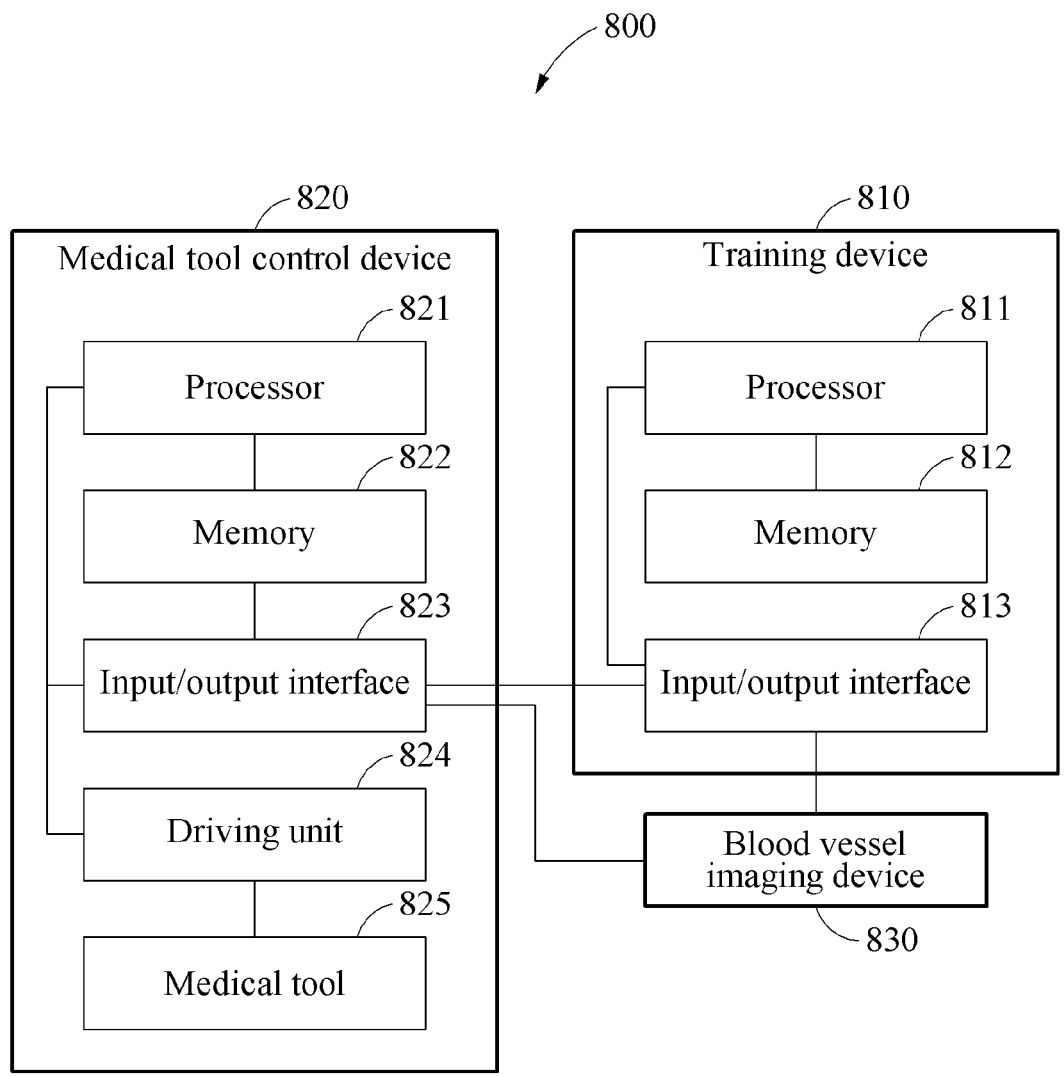
FIG. 8 is a block diagram illustrating a system for training a machine learning model for determining an operation command of a medical tool control device according to an example embodiment.

FIG. 8 is a block diagram illustrating a system for training a machine learning model for determining an operation command of a medical tool control device according to an example embodiment.

A system 800 for training a machine learning model according to an example embodiment may include a medical tool control device 820, a training device 810, and a blood vessel imaging device 830. The medical tool control device 820 may include a processor 821, a memory 822, an input/output interface, a driving unit 824, and a medical tool 825, and the training device 810 may include a processor 811, a memory 812, and an input/output interface. The medical tool control device 820, the training device 810, and the blood vessel imaging device each may perform each function with a separate housing, but are not limited thereto, and may perform each function with a single housing.

The processor 811 of the training device 810 according to an example embodiment may train the machine learning model by using the evaluation data calculated according to the position of the medical tool 825 in the blood vessel image. Since the training of the machine learning model has been described above, a detailed description thereof will be omitted. The memory 812 of the training device 810 may at least temporarily store at least one of guide data, operation commands, evaluation data, and a machine learning model, and the processor 811 may train the machine learning model by using the data stored in the memory 812. The input/output interface of the training device 810 may be connected to the medical tool control device 820 and the blood vessel imaging device 830 to transmit and receive data.

The processor 821 of the medical tool control device 820 according to an example embodiment may determine an operation of the driving unit 824 based on the operation command received from the training device 810. The memory 822 of the medical tool control device 820 may at least temporarily store the data received from the training device 810 or the blood vessel imaging device 830, and may transmit the data to the processor 821. The input/output interface of the medical tool control device 820 may be connected to the training device 810 and the blood vessel imaging device 830 to transmit and receive data. The driving unit 824 of the medical tool control device 820 may guide a medical tool 825 using a motor according to an operation command determined by the processor 821 of the medical tool control device 820.

The example embodiments described above may be implemented in hardware components, software components, and/or combinations of hardware components and software components. For example, the apparatus, the method, and the components described in the example embodiments may be implemented using, for example, one or more general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or other any devices capable of executing and responding instructions. The processing device may perform an operating system OS and one or more software applications performed on the operating system. In addition, the processing device may also access, store, manipulate, process, and generate data in response to execution of software. For convenience of understanding, one processing device may be described to be used, but it can be seen to those skilled in the art that the processing device may include a plurality of processing elements and/or a plurality of types of processing elements. For example, the processing device may include a plurality of processors or one processor and one controller. In addition, other processing configurations, such as a parallel processor are also possible.

Software may include computer programs, codes, instructions, or one or more combinations thereof, and may configure the processing device to operate as desired, or to instruct independently or collectively the processing device. Software and/or data may be permanently or temporarily embodied in any type of machines, components, physical devices, virtual equipment, computer storage media or devices, or signal waves to be transmitted, in order to be interpreted by the processing device or provide instructions or data to the processing device. The software may be distributed on a computer system connected via a network, and may be stored or executed in a distributed method. The software and data may be stored in one or more computer readable recording media.

The method according to the example embodiment may be implemented in a form of program instructions which may be performed through various computer means to be recorded in computer readable media. The computer readable media may include program instructions, data files, data structures, and the like alone or in combination. The program instructions recorded in the medium may be specially designed and configured for the example embodiments or may be publicly known to and used by those skilled in the computer software art. Examples of the computer readable media include magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program instructions. Examples of the program instructions include high language codes executable by a computer using an interpreter and the like, as well as machine language codes created by a compiler. The hardware devices may be configured to operate as one or more software modules in order to perform the operations of the example embodiments, and vice versa.

As described above, although the example embodiments have been described by the restricted drawings, various modifications and variations can be applied based on the example embodiments by those skilled in the art. For example, even if the described techniques are performed in a different order from the described method, and/or components such as a system, a structure, a device, a circuit, and the like described above are coupled or combined in a different form from the described method, or replaced or substituted by other components or equivalents, an appropriate result can be achieved.

The invention claimed is:

1. A method for training, by a processor, a machine learning model for determining an operation of a medical tool control device comprising steps of:
   Obtaining, by a processor, an operation command to move a medical tool of the medical tool control device based on the machine learning model from guide data generated using a blood vessel image;
   generating, by the processor, evaluation data of a position to which a distal end of the medical tool has been moved according to the operation command in the blood vessel image; and
   updating, by the processor, the machine learning model by changing a parameter of the machine learning model by using the evaluation data;
   wherein the processor generating of the evaluation data includes:
   applying a first group compensation value to the evaluation data in response to a case where the distal end of the medical tool reaches one of the destination area and the middle target area in the blood vessel image; and
   applying a second group compensation value to the evaluation data in response to a case where the distal end of the medical tool reaches a penalty area and a case where the distal end of the medical tool has been moved into a section between a middle target area, a destination area, or the penalty area.

2. The method for training the machine learning model of claim 1, wherein the processor generating of the evaluation data includes applying a compensation value calculated by evaluating the position to which the distal end of the medical tool has been moved in the blood vessel image based on the guide data to the evaluation data.

3. The method for training the machine learning model of claim 1, wherein the guide data includes information about the position of the distal end of the medical tool together with at least one of a middle target area, an access restriction point (a penalty area), and a destination area in a patch image corresponding to at least a partial area of the blood vessel image.

4. The method for training the machine learning model of claim 1, wherein the processor applying of the first group compensation value includes
applying a first compensation value to the evaluation data in response to the case of reaching the destination area; and
applying a second compensation value distinguished from the first compensation value to the evaluation data in response to the case of reaching the middle target area.

5. A non-transitory computer-readable recording medium storing one or more computer programs including instructions for performing the method of claim 1.

6. The method for training the machine learning model of claim 1, wherein the processor applying of the second group compensation value includes:
applying a third compensation value to the evaluation data in response to the case of reaching the penalty area; and
applying a fourth compensation value distinguished from the third compensation value in response to the case of moving into the section between the areas.

7. The method for training the machine learning model of claim 1, wherein the processor training of the machine learning model includes:
calculating an estimated evaluation value associated with an operation command output from a guide image corresponding to a current time frame by using the machine learning model;
calculating a measured evaluation value from a guide image corresponding to a next time frame after the distal end of the medical tool has been moved according to the operation command output in the current time frame; and
determining a parameter to update the machine learning model by using the estimated evaluation value and the measured evaluation value.

8. The method for training the machine learning model of claim 1, wherein the processor obtaining of the operation command of the medical tool control device includes:
calculating an expectation value to reach a destination area for each of candidate operation commands that may be performed by the medical tool control device by using the machine learning model; and
outputting an operation command having the highest expectation value among the candidate operation commands by using the machine learning model.

9. The method for training the machine learning model of claim 1, comprising:
obtaining, by the processor, a blood vessel structure from the blood vessel image;
setting a middle target area and a penalty area based on the blood vessel structure and the destination area;
obtaining an entire guide image in which the destination area, the middle target area, and the penalty area are set;
extracting partial guide information from the entire guide image based on the position of the distal end of the medical tool; and
determining the operation command based on the machine learning model from the partial guide information.

10. An apparatus for training a machine learning model comprising:
a processor configured to obtain an operation command for moving a medical tool of a medical tool control device based on the machine learning model for determining an operation of the medical tool control device from guide data generated using a blood vessel image, generate evaluation data for a position to which a distal end of the medical tool has been moved according to the operation command in the blood vessel image, and update the machine learning model by changing a parameter of the machine learning model by using the evaluation data; and
a memory configured to store at least one of the guide data, the operation command, the evaluation data, and the machine learning model,
wherein the processor applies a first group compensation value to the evaluation data in response to a case where the distal end of the medical tool reaches one of the destination area and the middle target area in the blood vessel image, and applies a second group compensation value in response to a case where the distal end of the medical tool reaches a penalty area and a case where the distal end of the medical tool has been moved into a section between a middle target area, a destination area, or the penalty area.

11. The apparatus for training the machine learning model of claim 10, wherein the processor obtains a blood vessel structure from the blood vessel image, sets a middle target area and a penalty area based on the blood vessel structure and a destination area, obtains an entire guide image in which the destination area, the middle target area, and the penalty area are set, extracts partial guide information from the entire guide image based on the position of the distal end of the medical tool, and determines the operation command based on the machine learning model from the partial guide information.

12. The apparatus for training the machine learning model of claim 10, wherein the processor applies a compensation value calculated by evaluating the position to which the distal end of the medical tool has been moved in the blood vessel image based on the guide data to the evaluation data.

13. The apparatus for training the machine learning model of claim 10, wherein the guide data includes information about the position of the distal end of the medical tool together with at least one of a middle target area, a penalty area, and a destination area in a patch image corresponding to at least a partial area of the blood vessel image.

14. The apparatus for training the machine learning model of claim 10, wherein the processor applies a first compensation value to the evaluation data in response to the case of reaching the destination area and applies a second compensation value distinguished from the first compensation value to the evaluation data in response to the case of reaching the middle target area.

15. The apparatus for training the machine learning model of claim 10, wherein the processor calculates an expectation value to reach a destination area for each of candidate operation commands that may be performed by the medical tool control device by using the machine learning model and outputs an operation command having the highest expectation value among the candidate operation commands by using the machine learning model.

16. The apparatus for training the machine learning model of claim 10, wherein the processor applies a third compensation value to the evaluation data in response to the case of reaching the penalty area and applies a fourth compensation value distinguished from the third compensation value in response to the case of moving into the section between the areas.

17. The apparatus for training the machine learning model of claim 10, wherein the processor calculates an estimated evaluation value associated with an operation command output from a guide image corresponding to a current time frame by using the machine learning model, calculates a measured evaluation value from a guide image corresponding to a next time frame of the moving result according to the operation command output in the current time frame, and determines the evaluation data by using the estimated evaluation value and the measured evaluation value.

\* \* \* \* \*